United States Patent [19]

Egrie

[11] Patent Number: 5,106,760
[45] Date of Patent: * Apr. 21, 1992

[54] ATCC HB8209, ITS MONOCLONAL ANTIBODY TO ERYTHROPOIETIN AND ASSAY USING SAME

[75] Inventor: Joan C. Egrie, Thousand Oaks, Calif.

[73] Assignee: Kirin-Amgen, Thousand Oaks, Calif.

[*] Notice: The portion of the term of this patent subsequent to Dec. 10, 2002 has been disclaimed.

[21] Appl. No.: 214,850

[22] Filed: Jun. 30, 1988

Related U.S. Application Data

[63] Continuation of Ser. No. 794,236, Nov. 1, 1985, abandoned, which is a continuation of Ser. No. 463,724, Feb. 4, 1983, Pat. No. 4,558,066.

[51] Int. Cl.$^5$ ............................................. G01N 33/53
[52] U.S. Cl. ................................... 436/518; 436/532; 436/536; 436/547; 436/548; 436/817; 435/7.1; 435/70.21; 435/172.2; 530/326; 530/329; 530/806; 530/387.9; 530/388.23; 935/102; 935/110
[58] Field of Search ............. 435/7, 68, 172.2, 240.27, 435/803, 810, 948; 436/518, 548, 817, 824; 530/324, 325, 349, 395, 412

[56] References Cited

U.S. PATENT DOCUMENTS

| | | | |
|---|---|---|---|
| 3,033,753 | 5/1962 | White et al. | 167/74 |
| 3,865,801 | 2/1975 | Chiba et al. | 260/112 |
| 4,376,110 | 3/1983 | David et al. | 436/548 |
| 4,423,147 | 12/1983 | Secher et al. | 435/68 |

OTHER PUBLICATIONS

Baron, et al., Cell, 28, 395–404 (1982).
Chisolm, High Technology, 3:1, 57–63 (1983).
Cotes, Nature, 191, 1065–1067 (1961).
Dreesman, et al., Nature, 295, 158–160 (1982).
Engvall et al., J. Immunology, 109, 129 (1972).
Lee-Huang, Fed. Proceedings, 41, p. 520, Abstract No. 1463 (1982).
Goding, J. Imm. Methods, 39, 285–308 (1980).
Green et al., Cell, 28, 477–487 (1982).
Hewick et al., J. Biol. Chem., 256, 7990–7997 (1981).
Hopp et al., Proc. Nat'l Acad. Sci. (U.S.A.), 78, 3824 (1981).
Kennett et al., eds., Monoclonal Antibodies, Hybridomas: A New Dimension in Biological Analyses, Plenum Press, New York, NY, pp. 403–404 (1980).
Lerner et al., Cell, 23, 309–310 (1981).
Lerner et al., Proc. Nat'l Acad. Sci. (U.S.A.), 78, 3403–3407 (1981).
Lerner, Scientific American, 248:12, 66–74 (1983).
Merrifield, J. American Chem. Soc., 85, 2149–2154 (1963).
Miyake et al., J. Bio. Chem., 252:15, 5558–5564 (1977).
Nigg, et al., Proc. Nat'l Acad. Sci. (U.S.A.), 79, 5322–5326 (1982).
Oi et al., in Selected Methods in Cellular Immunology, Mishell et al., eds., W. H. Freeman Publishing, San Francisco, CA, pp. 351–372 (1979).
O'Sullivan et al., Analytical Biochemistry, 100, 100–108 (1979).
Ross et al., Nature, 294, 654–656 (1981).
Schulman et al., Nature, 276, 269 (1978).
Sevier et al., Clin. Chem., 27:11, 1797–1806 (1981).
Stewart et al., Solid Phase Peptide Synthesis, San Fran., Calif., W. H. Freeman & Co., (1969) (Book-No Enclosed).
Walter et al., Proc. Nat'l Acad. Sci., (U.S.A.), 77, 5197–5200 (1980).
Walter et al., Proc. Nat'l Acad. Sci. (U.S.A.), 78, 4882–4886 (1981).
Weiss et al., Proc. Nat'l Acad. Sci. (U.S.A.), 79, 5465–5469 (1982).
Wong et al., Proc. Nat'l Acad. Sci. (U.S.A.) 78, 7412–7416 (1981).

Primary Examiner—Sam Rosen
Attorney, Agent, or Firm—Marshall, O'Toole, Gerstein, Murray, & Bicknell

[57] ABSTRACT

Disclosed is a new mouse-mouse hybridoma tumor cell line A.T.C.C. No. HB8209. A monoclonal antibody produced by said cell line is specifically immunologically reactive with erythropoietin and with a polypeptide whose amino acid sequence is substantially duplicative of a sequence extent in erythropoietin. Disclosed also are procedures for isolation of erythropoietin by affinity purification and for quantitative detection of erythropoietin in fluid samples.

5 Claims, No Drawings

ATCC HB8209, ITS MONOCLONAL ANTIBODY TO ERYTHROPOIETIN AND ASSAY USING SAME

This is a continuation of U.S. application Ser. No. 794,236, filed Nov. 1, 1985 and now abandoned, which, in turn, was a continuation of U.S. application Ser. No. 463,724, filed Feb. 4, 1983 and issued as U.S. Pat. No. 4,558,006 on Dec. 10, 1985.

BACKGROUND OF THE INVENTION

The present invention relates generally to materials and methods for use in immunological procedures for quantitative detection and isolation of the hormone erythropoietin in fluid samples. More specifically, the invention relates to a monoclonal anti-erythropoietin antibody produced by a novel tumor cell line A.T.C.C. HB8209. The antibody is immunologically reactive with a low molecular weight polypeptide having an amino acid sequence substantially duplicative of a sequence extant in erythropoietin. The antibody is useful in diagnostic assays on human fluids and in procedures for affinity purification and isolation of human erythropoietin.

Erythropoiesis, the production of red blood cells, occurs continuously throughout the human life span to offset cell destruction. Erythropoiesis is a very precisely controlled physiological mechanism enabling sufficient numbers of red blood cells to be available in the blood for proper tissue oxygenation, but not so many that the cells would impede circulation. The formation of red blood cells occurs in the bone marrow and is under the control of the hormone, erythropoietin.

Erythropoietin, an acidic glycoprotein of approximately 34,000 molecular weight, may occur in three forms: $\alpha$, $\beta$, and asialo. The $\alpha$ and $\beta$ forms differ slightly in carbohydrate components, but have the same potency, biological activity and molecular weight. The asialo form is an $\alpha$ or $\beta$ form with the terminal carbohydrate (sialic acid) removed. Erythropoietin is present in very low concentrations in plasma when the body is in a healthy state wherein tissues receive sufficient oxygenation from the existing number of erythrocytes. This normal low concentration is enough to stimulate replacement of red blood cells which are lost normally through aging.

The amount of erythropoietin in the circulation is increased under conditions of hypoxia when the number of red blood cells in the circulation is reduced. Hypoxia may be caused by loss of large amounts of blood through hemorrhage, destruction of red blood cells by over-exposure to radiation, reduction in oxygen intake due to high altitudes or prolonged unconsciousness, or various forms of anemia. In response to tissues undergoing hypoxic stress, erythropoietin will increase red blood cell production by stimulating the conversion of primitive precursor cells in the bone marrow into pro-erythroblasts, bone marrow cells which subsequently mature, synthesize hemoglobin and are released into the circulation as red blood cells. When the number of red blood cells in circulation is greater than needed for normal tissue oxygen requirements, erythropoietin in circulation is decreased.

Because erythropoietin is essential in the process of red blood cell formation, the hormone has potential useful application in both the diagnosis and the treatment of blood disorders characterized by low or defective red blood cell production. Prior attempts to obtain erythropoietin in good yield from plasma or urine, however, have proven relatively unsuccessful. Complicated and sophisticated laboratory techniques are necessary and generally result in the collection of very small amounts of impure and unstable extracts containing erythropoietin.

U.S. Pat. No. 3,033,753 describes a method for partially purifying erythropoietin from sheep blood plasma which provides low yields of a crude solid extract containing erythropoietin.

Initial attempts to isolate erythropoietin from urine yielded unstable, biologically inactive preparations of the hormone. U.S. Pat. No. 3,865,801 describes a method of stabilizing the biological activity of a crude substance containing erythropoietin recovered from urine. The resulting crude preparation containing erythropoietin purportedly retains 90% of erythropoietin activity, and is stable.

Another method of purifying human erythropoietin from urine of patients with aplastic anemia is described in Miyake, et al., *J. Biol. Chem.*, Vol. 252, No. 15 (Aug. 10, 1977), pp. 5558-5564. This seven-step procedure includes ion exchange chromatography, ethanol precipitation, gel filtration, and adsorption chromatography, and yields a crude erythropoietin preparation with a potency of 70,400 units/mg of protein in 21% yield. The purified hormone has a single electrophoretic component in polyacrylamide gels at pH 9, in the presence of sodium dodecyl sulfate at pH 7, and in the presence of Triton X-100 at pH 6. Two fractions of the same potency and molecular size, by sodium dodecyl sulfate gel electrophoresis, but differing slightly in mobility at pH 9, are obtained at the last step of fractionation.

Other techniques utilized to obtain purified erythropoietin involve immunological procedures. A polyclonal, serum-derived antibody directed against erythropoietin is developed by injecting an animal, preferably a rat or rabbit, with human erythropoietin. The injected human erythropoietin is recognized as a foreign antigenic substance by the immune system of the animal and elicits production of antibodies against the antigen. Differing cells responding to stimulation by the antigenic substance produce and release into circulation antibodies slightly different from those produced by other responding cells. The antibody activity remains in the serum of the animal when its blood is extracted. While unpurified serum or antibody preparations purified as a serum immunoglobulin G fraction may then be used in assays to detect and complex with human erythropoietin, the materials suffer from a major disadvantage. This serum antibody, composed of all the different antibodies produced by individual cells, is polyclonal in nature and will complex with components in crude extracts other than erythropoietin alone.

Of interest to the background of the present invention are recent advances in the art of developing continuous cultures of cells capable of producing a single species of antibody which is specifically immunologically reactive with a single antigenic determinant of a selected antigen. See, generally, Chisholm, *High Technology*, Vol. 3, No. 1, 57-63 (1983). Attempts have been made to employ cell fusion and hybridization techniques to develop "monoclonal" antibodies to erythropoietin and to employ these antibodies in the isolation and quantitative detection of human erythropoietin. As one example, a report of the successful development of mouse-mouse hybridoma cell lines secreting monoclonal antibodies to human erythropoietin appeared in abstract form in Abstract No. 1463 of *Fed. Proc.*, 41, 520 (1982). As another example, a detailed description of the preparation and use of a monoclonal, anti-erythropoietin antibody appears in Weiss, et al., *P.N.A.S. (U.S.A.)*, 79, 5465–5469 (1982).

To the extent that the two above-noted publications may provide access to monoclonal antibodies useful in the efficient isolation of erythropoietin by immunological affinity purification and the accurate quantitative detection of erythropoietin by immunobinding assays, such purifications and assays will nonetheless be prey to the problems which typically beset other immunological procedures relating to other biologically active proteinaceous materials. As one example, a common problem in most procedures for affinity purification of proteinaceous materials (whether monoclonal or polyclonal antibodies are used) is that harshly acidic or basic solutions are needed to elute the protein bound to the immobilized antibody. Frequently elution conditions diminish or destroy the biological activity of the material to be isolated. As another example, where immunobinding assays are employed in quantitative detection of a proteinaceous material in a fluid sample, the amount of material present in the sample is usually determined by comparison of the extent of an immunobinding reaction of the antibody to a "standard" solution including a fixed quantity of the same proteinaceous material in pure form. One example of such an assay is a competition reaction wherein proteinaceous material competes for the antibody in the presence of a "standard" solution including a fixed quantity of the same proteinaceous material in pure form. Quantification of the competition reaction is made by comparison to the extent of reaction of the antibody with increasing quantities of pure standard. Where, as in the case of erythropoietin, the material to be assayed is a rather labile substance which is easily destroyed in processes (including radiolabelling processes) for generating and storing standard solutions, the accuracy of the entire assay system can be severely compromised.

Also of interest to the background of the invention are reports of the immunological activity of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically significant proteins such as viral antigens, polypeptide hormones and the like. Included among the immune reactions of such polypeptides is the provocation of the formation of specific antibodies in immunologically active animals. See, e.g., Lerner, et al., *Cell*, 23, 309–310 (1981); Ross, et al., *Nature*, 294, 654–656 (1981); Walter, et al., *P.N.A.S. (U.S.A.)*, 77, 5197–5200 (1980); Lerner, et al., *P.N.A.S. (U.S.A.)*, 78, 3403–3407 (1981); Walter, et al., *P.N.A.S. (U.S.A)*, 78, 4882–4886 (1981); Wong, et al., *P.N.A.S. (U.S.A.)*, 78, 7412–7416 (1981); Green, et al., *Cell*, 28, 477–487 (1982); Nigg, et al., *P.N.A.S. (U.S.A.)*, 79, 5322–5326 (1982); Baron, et al., *Cell*, 28, 395–404 (1982); Dreesman, et al., *Nature*, 295, 158–160 (1982); and Lerner, *Scientific American*, 248, No. 2, 66–74 (1983). The above studies relate, of course, to amino acid sequences of proteins other than erythropoietin, a substance for which no substantial amino acid sequence information has been published.

Despite recent substantial advances in the art, there continues to exist a substantial need in the art for further new methods and materials useful in obtaining large quantities of pure, biologically active erythropoietin from plasma or urine and methods and materials useful in the accurate quantitative detection of erythropoietin in human fluid samples.

BRIEF SUMMARY

The present invention provides a new mouse-mouse hybridoma cell line A.T.C.C. No. HB8209. This cell line secretes into the media as a product of its growth a highly specific monoclonal, anti-erythropoietin antibody which is also specifically immunoreactive with a polypeptide comprising the following sequence of amino acids: $NH_2$-Ala-Pro-Pro-Arg-Leu-Ile-Cys-Asp-Ser-Arg-Val-Leu-Glu-Arg-Tyr-Leu-Leu-Glu-Ala-Lys-COOH. The antibody produced by A.T.C.C. HB8209 is thus the first antibody substance ever demonstrated to be immunoreactive with both erythropoietin and a polypeptide substantially duplicative of the amino acid sequence extant in erythropoietin. Tumor cell line, A.T.C.C. HB8209, is on deposit at the American Type Culture Collection, 12301 Parklawn Drive, Rockville, Md. 20852.

According to the invention the IgG1 antibody produced by A.T.C.C. HB8209 is advantageously employed in immunological procedures for the isolation of large quantities of pure, biologically active erythropoietin and in diagnostic immunoassays for the quantitative detection of erythropoietin in fluid samples.

The antibody substances provided by the invention facilitate performance of assays for quantitative detection of erythropoietin in fluid samples (such as blood, serum, urine, cystic fluid and cerebrospinal fluid), especially those assays which require the use of two antibodies which are immunoreactive with two different antigenic determinants of erythropoietin. In such procedures, a first antibody (e.g., that produced by A.T.C.C. No. HB8209) is immobilized on a solid support and, when contacted with the sample fluid, immunobinds to one antigenic determinant of the erythropoietin in the fluid. A second antibody (e.g., a polyvalent, serum-derived antibody or one of the monoclonal antibodies heretofore described in the art) which has preferably been linked to a detectable label is contacted with the complex of erythropoietin with the first antibody and binds to a different antigenic determinant of erythropoietin. The quantity of erythropoietin in the sample is thereafter determined through quantification of the bound second antibody.

Methods and materials of the present invention constitute significant advances in procedures for quantitative detection and affinity purification of selected proteinaceous materials. One such aspect of the invention is the provision of improved immunoassays for quantitative detection of a selected proteinaceous material in a fluid sample wherein the sample is contacted with an antibody capable of an immunobinding reaction with the proteinaceous material and wherein the amount of the proteinaceous material in the sample is determined by comparison of (a) the extent of immunobinding reaction of the antibody with sample components, to (b) the extent of immunobinding reaction of the antibody with a fixed quantity of a standard substance. The improvement of the invention comprises employing as the antibody a monoclonal antibody immunoreactive with both the selected proteinaceous material and with a relatively lower molecular weight polypeptide "fragment" substantially duplicative of an amino acid sequence extant in the proteinaceous material and thereafter employing the polypeptide as the standard substance. This improved immunoassay method is specifically applicable to detection of erythropoietin through use of the antibody produced by A.T.C.C. No. HB8209.

Another such aspect of the invention is an improved process for affinity purification and isolation of a selected proteinaceous material from a fluid which provides significant advantages in maintenance of biological activity of the substance isolated. The steps of the improved process include:

(1) immobilizing on a solid substrate a monoclonal antibody immunoreactive with the selected proteinaceous material and with a polypeptide "fragment" which is substantially duplicative of a sequence of amino acids extant in the proteinaceous material, with the antibody further characterized as having a higher immunological affinity for the polypeptide fragment than for the proteinaceous material;

(2) contacting the fluid with the immobilized antibody, whereby the selected proteinaceous material is immobilized through immunobinding to the antibody; and (3) eluting the proteinaceous material from immunobinding association with the immobilized antibody by means of contact with a solution of polypeptide for which the antibody has a higher immunological affinity.

Because the eluting procedure can be carried out under substantially the same pH and temperature conditions as the initial immunobinding procedure, the proteinaceous material isolated (through displacement by the polypeptide) is more likely to retain the full extent of its biological and chemical properties and activities. Due to the higher affinity of the monoclonal antibody produced by A.T.C.C. No. HB8209 for the previously-specified polypeptide as compared to erythropoietin, this improved affinity purification is specifically applicable to erythropoietin isolations.

Other aspects and advantages of the present invention will be apparent upon consideration of the following detailed description of preferred embodiments thereof.

DETAILED DESCRIPTION

The following examples illustrate practice of the invention in the production of hybridoma cell line A.T.C.C. No. HB8209 and the isolation of monoclonal antibodies to both erythropoietin and a lower molecular weight (20-mer) polypeptide duplicative of sequences of amino acids extant in erythropoietin at its amino terminal. Also illustrated is the characterization, amplification and determination of properties of antibodies produced by A.T.C.C. No. HB8209.

EXAMPLE 1

Development of Amino Acid Sequences and Synthetic Peptide

Erythropoietin was isolated according to the method of Miyake, et al., *J. Biol. Chem.*, 252, 5558-5564 (1977) and amino acid analysis was performed by the gas phase sequencer (Applied Biosystems, Inc.) according to the procedure of Hewick, M., et al., *J. Biol. Chem.*, 256, 7990-7997 (1981). The sequence revealed for the first twenty amino acids of the amino terminal end of the glycoprotein was as follows:

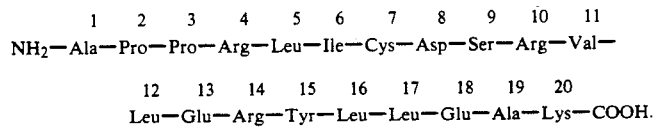

Analysis of the sequence by the method of Hopp, et al., *P.N.A.S. (U.S.A.)*, 78, 3824 (1981) reveals that the sequence of amino acids spanning residues 9 through 14 (Ser-Arg-Val-Leu-Glu-Arg) is significantly hydrophilic and hence likely to have substantial antigenic potential.

A synthetic replica of the above-noted 20-mer was prepared according to the procedure of Merrifield, R. B., *J. of Am. Chem. Soc.*, 85, 2149-2154 (1963) [see also, Stewart, J. M., et al., *Solid Phase Peptide Synthesis*, San Francisco: W. H. Freeman & Co. (1969)] and covalently crosslinked using m-Maleimidobenzoyl-N-hydroxysuccinimide ester (Pierce Chemical Corp.) to a keyhole limpet hemocyanin (KLH) carrier protein, according to the procedure of O'Sullivan, et al., *Analytical Biochemistry*, 100, 100-108 (1979).

EXAMPLE 2

Hybridoma Production

In the procedure for production of hybridoma cell line A.T.C.C. No. HB8209, BALB/C mice (Simonsen Laboratories, Gilroy, Calif.) were hyperimmunized to the KLH-bound synthetic polypeptide prepared according to Example 1. The immunization and cell fusion procedures were performed according to essentially standard procedures set out in Oi, et al., pp. 351-372 in *Selected Methods in Cellular Immunology* (Mishell, et al., eds.), W. H. Freeman Publishing, San Francisco (1979). The first inoculation was subcutaneous and contained 10 micrograms of uncrosslinked 20-mer synthetic peptide plus Difco HRa Complete Adjuvant (Difco Laboratories). Further inoculations were given intraperitoneally 12, 26 and 37 days after the subcutaneous injection, each containing 10 micrograms of crosslinked 20-mer synthetic peptide. Three days prior to cell fusion, the mice were inoculated with a final intraperitoneal injection containing 15 micrograms of crosslinked 20-mer synthetic peptide.

After the five injections, serum from several mice was assayed by a radioimmunoprecipitation (RIP) assay and tested positively for the presence of serum antibodies to both $^{125}$I-erythropoietin and $^{125}$I-labelled synthetic peptide. Disassociated immunoprecipitant and pure $^{125}$I-erythropoietin were subjected to electrophoresis on 12.5% sodium dodecyl sulfate polyacrylamide gel (SDS-PAGE). Autoradiographs of the gels indicate that both the disassociated immune complex and the labelled $^{125}$I-erythropoietin migrated identically. Immune serum also successfully inhibited erythropoietin activity in a bioassay [Cotes, *Nature*, 191, 1065-1067 (1961)].

Following verification that the inoculated mice were producing serum antibodies to erythropoietin and the synthetic polypeptide, spleens of the immunized BALB/C mice, which contain a small number of antibody-producing lymphocytes, are disrupted to single cells. In the presence of the fusogen polyethylene glycol, immune donor spleen cells are fused with a parental BALB/C myeloma cell line, SP2/0-[HPRT$^-$] [Schulman, et al., *Nature*, 276, 269 (1978)] to produce a variety of hybrids. Briefly described, cell membranes fuse and initially surround a common cytoplasm with two or more nuclei. Several days after that event, the nuclei fuse and become capable of synchronous mitosis. As these fused cells divide, a variable number of chromosomes of both rused partners are lost until the hybrid cell lines stabilize.

Fused cells are plated into five multiple 96-well plates (445 total wells) at $10^5$ to $10^6$ cells per well. Selection of SP2/0:spleen cell hybrids from the fusion which also produces SP2/0:SP2/0 and spleen:spleen cell hybrids is accomplished by culturing the fusion mixture in hypoxanthine-aminopterin-thymidine (HAT) medium for two weeks. HAT medium prevents SP2/0:SP2/0 hybrids from dividing. The spleen:spleen cell hybrids generally die after two weeks in culture. Thus the HAT medium allows growth of only the SP2/0:spleen hybrid cells.

After 10 days, 445 wells contained multiple, viable cell colonies. Thereafter the individual cell colonies were screened for the presence of immunoglobulins and erythropoietin-specific antibodies.

EXAMPLE 3

Screening, Cloning and Characterization of Monoclonal Antibodies

A radioimmunoprecipitation assay as in Example 2 was performed to reveal specific anti-erythropoietin, anti-polypeptide antibodies in the wells. The results of these two screening assays showed that 60 of the 445 initial wells were positive for anti-polypeptide antibody. Of these 60, 3 tested positively for immunoreactivity with $^{125}$I-erythropoietin.

Cells from each of the three initially screened colonies were further subdivided into several multi-well plates (about ten cells per well), and allowed to grow. These wells were again screened by radioimmunoprecipitation for the presence of both anti-polypeptide and anti-erythropoietin antibody. Only one of the initial three positive wells yielded stable antibody-producing clones after the first subcloning step.

Cells from the strongest positive well from the first subcloning were diluted into new plates at a calculated density of 1 cell per 5 wells. The low density assures that a high proportion of colonies will derive from a single cell. Thereafter culture fluids from all wells were assayed by radioimmunoprecipitation in the procedures described above. The results of this cloning procedure produced eleven possibly equivalent, strongly positive single-cell colonies producing antibody to both the polypeptide and erythropoietin and having satisfactory cell growth rate and density. One of these cell lines was selected for deposit as A.T.C.C. No. HB8209.

An ELISA [See, Engvall and Perlman, *J. Immunology*, 109, 129 (1972)] performed on culture fluids of A.T.C.C. No. HB8209 characterized the clone as producing antibody of the IgG1 subclass.

To assess the ability of the clone culture fluid to precipitate labelled $^{125}$I-erythropoietin and $^{125}$I-polypeptide, a radioimmunoprecipitation assay was performed and revealed that the monoclonal antibody produced by A.T.C.C. No. HB8209 had an approximately 8- to 10- fold greater affinity for the polypeptide as for erythropoietin.

To isolate maximum antibody producing cells, A.T.C.C. No. HB8209 cells are continuously subcultured to avoid deleterious effects of aging. A desirable medium for growth of hybridoma cells is HB101 (Hanna Biologicals) supplemented with 1% fetal calf serum (Tissue Culture Biologicals); when cells are in condition for harvesting culture fluid, the medium is preferably changed to HB101 without fetal calf serum.

Monoclonal antibodies may be isolated from culture fluids by AMICON filtration concentration (Amicon), followed by precipitation with ammonium sulfate. Alternatively, the concentrated culture fluids may be adsorbed to Protein A-Sepharose columns (Pharmacia Corp.). [See, Goding, *J. Imm. Methods*, 39, 285–308 (1980)]. In these columns, the Protein A attaches to the Fc portion of the antibody immunoglobulin, allowing other contaminants in the culture fluid to elute out of association with the antibody. Although column capacity for mouse IgG1 is low, nonetheless, the antibody achieves considerable purification by this method.

EXAMPLE 4

Amplification of Antibody Yields by Ascites Method

To obtain a more concentrated antibody than that produced in tissue culture, the monoclonal antibodies of the present invention may be amplified by the ascites method generally described in Kenneth, et al., (eds.), *Monoclonal Antibodies, Hybridomas: A New Dimension in Biological Analysis*, p. 403, New York: Plenum Press (1981). According to this procedure, $3 \times 10^6$ to $3 \times 10^7$ hybridoma cells may be injected into the peritoneal cavities of BALB/C mice, previously treated with 0.25 ml Pristane (Aldrich Chemical Co.). Pristane treatment permits growth of tumor cells in an ascitic form within the peritoneal cavity. Once the ascitic tumor cells grow, the mice are sacrificed and the ascitic fluid containing the monoclonal antibody is harvested from the cells by centrifugation. The monoclonal antibody in the ascites fluid is then assayed for antibody titer. Ascites fluid antibodies can be further purified from ascites fluid albumin by 40% ammonium sulfate precipitation and ion exchange chromatography.

EXAMPLE 5

Isolation of Erythropoietin

Through its provision of highly specific and highly reactive anti-erythropoietin monoclonal antibodies, the present invention makes possible the isolation of large quantities of erythropoietin from biological fluids such as blood, serum, urine, cystic fluid and cerebrospinal fluid by affinity purification procedures well known in the art. Briefly put, preferred isolation procedures would involve immobilizing an antibody of the invention on a solid support (e.g., a chromatographic column), contacting the erythropoietin containing fluid with the immobilized antibody and thereafter eluting purified erythropoietin from immune complex association with the antibody.

As indicated previously, the substantially higher affinity of the antibodies produced by A.T.C.C. No. HB8209 for the synthetic polypeptide employed in the generation of the hybridoma cell line as opposed to erythropoietin, makes it possible for erythropoietin to be isolated from immunobound form by treatment of the complex with a solution of the polypeptide rather than through use of harsh reagents and reaction conditions. This should result in better retention of biological activity for the isolated erythropoietin. Further, it is likely that such an "isolation by immunological displacement" may be effected through use of a polypeptide fragment which is smaller than the 20-mer used in hybridoma preparation. A likely candidate for this purpose would be a polypeptide of the formula RNH-Ala-Pro-Pro-Arg-Leu-Ile-Cys-Asp-Ser-Arg-Val-Leu-Glu-Arg-Tyr-Leu-Leu-Glu-Ala-Lys-COOR', wherein R and R' are the same or different and are selected from the group consisting of hydrogen or one or more amino acid residues. Such a sequence may be seen to include the highly hydrophilic sequence (Ser-Arg-Val-Leu-Glu-Arg) designated in Example 1 and is thus likely to be the specific antigenic site for the monoclonal antibody produced by A.T.C.C. HB8209.

EXAMPLE 6

Quantitative Detection of Erythropoietin

Through its provision of highly specific antierythropoietin monoclonal antibodies, the present invention also makes possible novel assays for quantitative detection of erythropoietin in a biological fluid sample which employ more than one antibody. Such assays would include the steps of:

(1) contacting the fluid with a first, immobilized antibody which reacts with a first antigenic determinant of erythropoietin in the fluid to form an immunological complex of erythropoietin and the first antibody;

(2) contacting the complex formed in step (1) with a second antibody which reacts with an antigenic determinant of erythropoietin other than the first antigenic determinant, to form an immunological complex of erythropoietin and the second antibody; and (3) quantifying the amount of the second antibody bound to the immunological complex formed in step (2).

In such assays, one of the antibodies (preferably the first antibody) would be the monoclonal antibody produced by A.T.C.C. No. HB8209. The second antibody could be another monoclonal, anti-erythropoietin antibody (such as already reported in the art) or a polyvalent, serum-derived antibody.

As previously noted, the provision of a monoclonal antibody which is selectively immunoreactive with both erythropoietin and with a polypeptide duplicative of an erythropoietin polypeptide sequence fragment provides a significant improvement in prior processes for quantitative detection of erythropoietin. Where ordinarily an immunobinding reaction of sample erythropoietin with an antibody is compared with an immunobinding reaction of the antibody with a fixed or standardized quantity of pure erythropoietin (or compared after competition with a fixed quantity of erythropoietin-containing standard to reaction of the antibody with increasing concentrations of pure erythropoietin) for purposes of quantifying the amount of erythropoietin in the sample, the antibody employed may be that produced, e.g., by A.T.C.C. No. HB8209 and the "standard" could be a polypeptide (the 20-mer used in hybridoma formation or a fragment thereof such as noted in Example 5) rather than erythropoietin. Such a procedure would eliminate the need for a continuing supply of erythropoietin as a standard, and diminish the loss of accuracy in detection which could be expected to accompany use of pure erythropoietin as a standard in the immunoassay.

Numerous modifications and variations in practice of the invention are expected to occur to those skilled in the art upon consideration of the foregoing descriptions of preferred embodiments thereof. Consequently, only such limitations should be placed upon the scope of the invention as appear in the appended claims.

What is claimed is:

1. A monoclonal antibody specifically immunoreactive with erythropoietin and with a polypeptide having the following amino acid sequence,
    NH$_2$-Ala-Pro-Pro-Arg-Leu-Ile-Cys-Asp-Ser-Arg-Val-Leu-Glu-Arg-Tyr-Leu-Leu-Glu-Ala-Lys-COOH.

2. An immunological assay for quantitative detection of erythropoietin in a biological fluid sample comprising the steps of:

(1) contacting said fluid with a first, immobilized antibody which reacts with a first antigenic determinant of erythropoietin in said fluid to form an immunological complex of erythropoietin and said first antibody;

(2) contacting the complex formed in step (1) with a second antibody which reacts with an antigenic determinant of erythropoietin other than said first antigenic determinant to form an immunological complex of erythropoietin and said second antibody;

(3) quantifying the amount of said second antibody bound to said immunological complex formed in step (2); and (4) estimating the quantity of erythropoietin in said sample based on the quantity of said bound second antibody, either said first or said second antibody ccmprising a monoclonal antibody of claim 1.

3. The assay of claim 2 wherein said first antibody or said second antibody is a polyvalent, serum-derived antibody.

4. In an immunoassay for quantitative detection of erythropoietin in a fluid sample wherein said sample is contacted with an antibody capable of an immunobinding reaction with erythropoietin and wherein the amount of erythropoietin in said sample is determined by comparison of (a) the extent of immunobinding reaction of said antibody with sample components, to (b) the extent of immunobinding reaction of said antibody with a fixed quantity of a standard substance, the improvement comprising:

employing as said antibody a monoclonal antibody according to claim 1; and employing as said standard substance a polypeptide consisting essentially of the amino acid sequence Serine-Arginine-Valine-Leucine-Glutamic Acid-Arginine and having the following amino acid sequence, RNH-Ser-Arg-Val-Leu-Glu-Arg-COOR', wherein R and R' are the same or different and are selected from the group consisting of hydrogen and one or more amino acid residues.

5. An improved process according to claim 4 wherein the amino acid sequence of said polypeptide comprises: RNH-Ala-Pro-Pro-Arg-Leu-Ile-Cys-Asp-Ser-Arg-Val-Leu-Glu-Arg-Tyr-Leu-Leu-Glu-Ala-Lys-COOR', wherein R and R' are the same or different and are selected from the group consisting of hydrogen and one or more amino acid residues.

* * * * *